United States Patent
Belkin et al.

(10) Patent No.: US 8,869,602 B2
(45) Date of Patent: Oct. 28, 2014

(54) HIGH FREQUENCY DEFLECTION MEASUREMENT OF IR ABSORPTION

(75) Inventors: Mikhail Belkin, Austin, TX (US); Feng Lu, Austin, TX (US); Vladislav V. Yakolev, College Station, TX (US); Craig Prater, Santa Barbara, CA (US); Kevin Kjoller, Santa Barbara, CA (US); Markus Raschke, Boulder, CO (US)

(73) Assignee: Anasys Instruments Corp., Santa Barbara, CA (US)

( * ) Notice: Subject to any disclaimer, the term of this patent is extended or adjusted under 35 U.S.C. 154(b) by 411 days.

(21) Appl. No.: 13/307,464

(22) Filed: Nov. 30, 2011

(65) Prior Publication Data

US 2012/0167261 A1    Jun. 28, 2012

Related U.S. Application Data (63) Continuation-in-part of application No. 13/135,956, filed on Jul. 18, 2011, now Pat. No. 8,607,622, which is a continuation of application No. 11/803,421, filed on May 15, 2007, now Pat. No. 8,001,830.

(51) Int. Cl.
*G01B 5/28* (2006.01)
*G01Q 20/02* (2010.01)

(52) U.S. Cl.
CPC .................................... *G01Q 20/02* (2013.01)
USPC ............................................ 73/105; 850/56

(58) Field of Classification Search
CPC ................................ G01Q 1/00; G01Q 20/02
USPC ............................................................ 73/105
See application file for complete search history.

(56) References Cited

U.S. PATENT DOCUMENTS

| 5,465,046 A * | 11/1995 | Campbell et al. ............ 324/244 |
| 7,572,300 B2 * | 8/2009 | Cohen et al. .................... 850/58 |
| 2009/0119808 A1 * | 5/2009 | Giakos ............................ 850/31 |

* cited by examiner

*Primary Examiner* — Hezron E Williams
*Assistant Examiner* — Rodney T Frank
(74) *Attorney, Agent, or Firm* — Mark Rodgers (57) ABSTRACT

An AFM based technique has been demonstrated for performing highly localized IR spectroscopy on a sample surface by using the AFM probe to detect wavelength dependent IR radiation interaction, typically absorption with the sample in the region of the tip. The tip may be configured to produce electric field enhancement when illuminated by a radiation source. This enhancement allows for significantly reduced illumination power levels resulting in improved spatial resolution by confining the sample-radiation interaction to the region of field enhancement which is highly localized to the tip.

30 Claims, 10 Drawing Sheets

HIGH FREQUENCY DEFLECTION MEASUREMENT OF IR ABSORPTION

RELATED APPLICATIONS

This Application is a Continuation-in-Part of U.S. application Ser. No. 13/135,956, filed Jul. 18, 2011 now U.S. Pat. No. 8,607,622 which in turn is a Continuation of U.S. application Ser. No. 11/803,421 filed May 15, 2007 now U.S. Pat. No. 8,001,830.

FEDERALLY SPONSORED RESEARCH

Not Applicable

SEQUENCE LISTING

Not Applicable

BACKGROUND OF THE INVENTION

This invention is related to highly localized infrared (IR) spectra and chemical mapping on a sample surface utilizing an Atomic Force Microscope (AFM) and a variable wavelength pulsed IR source illuminating the sample in the region of the AFM probe tip and producing a measurable wavelength dependent radiation-sample interaction, and in particular using an electric field enhancing probe tip to produce tip-sample interaction at lower power levels leading to improved spatial resolution.

IR spectroscopy is a useful tool in many analytical fields such as polymer science and biology. It would be particularly useful to perform IR spectroscopy on a highly localized scale, on the order of biological organelles or smaller, at various points on a sample surface. Such a capability would provide information about the composition of surfaces, such as location of different materials or molecular structures. Recently, a technique based on use of an AFM in a unique fashion to produce such localized spectra has been developed. This work was described in a publication entitled "Local Infrared Microspectroscopy with Sub-wavelength Spatial Resolution with an Atomic Force Microscope Tip Used as a Photothermal Sensor" Optics Letters, Vo. 30, No. 18, Sep. 5, 2005 and related publications by Dazzi et al. In addition, recent improvements have been described by Lu and Belkin as described in F. Lu, and M. A. Belkin, "Infrared absorption nano-spectroscopy using sample photoexpansion induced by tunable quantum cascade lasers," Optics Express 19, 19942 (2011), which is incorporated by reference. Those skilled in the art will comprehend the details of the technique in the publications but the technique will be described briefly herein for clarity.

Figure 1:
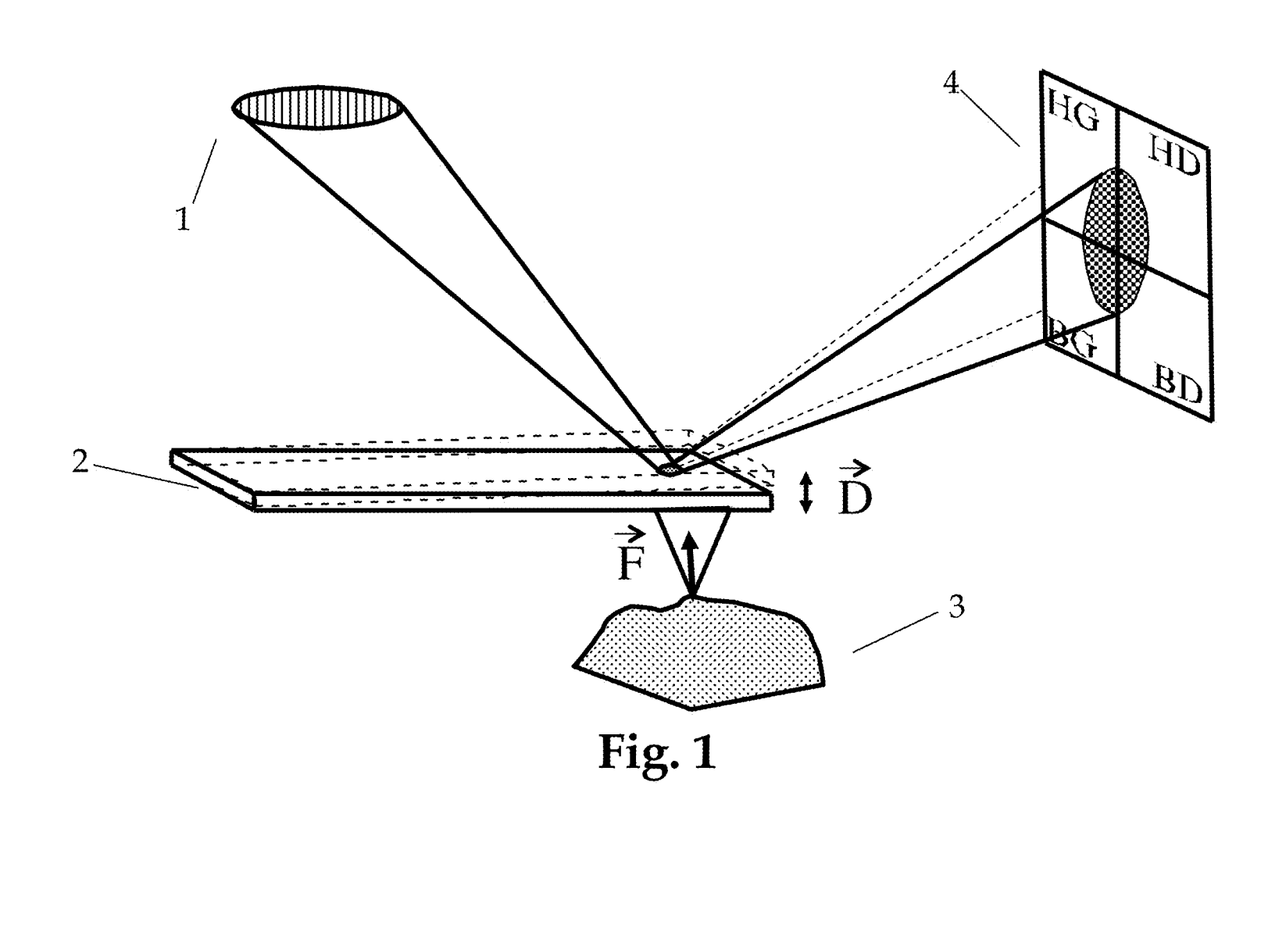
FIG. 1 shows schematically the operation of an AFM

AFM's are known in the art. The important aspects of an AFM for the current invention are shown in FIG. 1. A light beam 1 is directed at an angle to a cantilever arm 2 which reflects the beam to a photo-detector 4. Typically the photo-detector is a 4-quadrant type, and when the cantilever is placed in the AFM the lever is positioned such that the reflected beam is centered on the photo-detector. The cantilever typically has a probe tip that interacts with sample 3. The interaction can be contact, intermittent contact, non-contact including attractive and/or repulsive forces. Deflection of the cantilever vertically due to contact with the sample causes the beam spot to move on the detector, generating a difference signal from the detector quadrants. This type of AFM setup is called an optical lever arm, and commercially available AFM's using this technique can measure deflections of the lever on a sub-angstrom scale. There are other options to detect the deflection of the cantilever which can also be used, such as optical interferometry. Other deflection detectors may not generate as much information from the sample as the beam deflection detection. Not shown, but typically present in an AFM, is a scanner to generate relative movement between the tip and sample, and feedback electronics which typically servo the sample or tip up and down in response to height variations of the sample to maintain a desired interaction between the tip and sample. This vertical servo signal vs lateral position creates a topographical map of the surface which in, commercial AFM's, can attain atomic resolution. A wide variety of variations of the AFM exist with different types of probes and so on for measurements other than topography. For instance, in a co-pending application by some of the inventors of this application, a version of an AFM configured to measure thermal properties of a surface is described.

Figure 2:
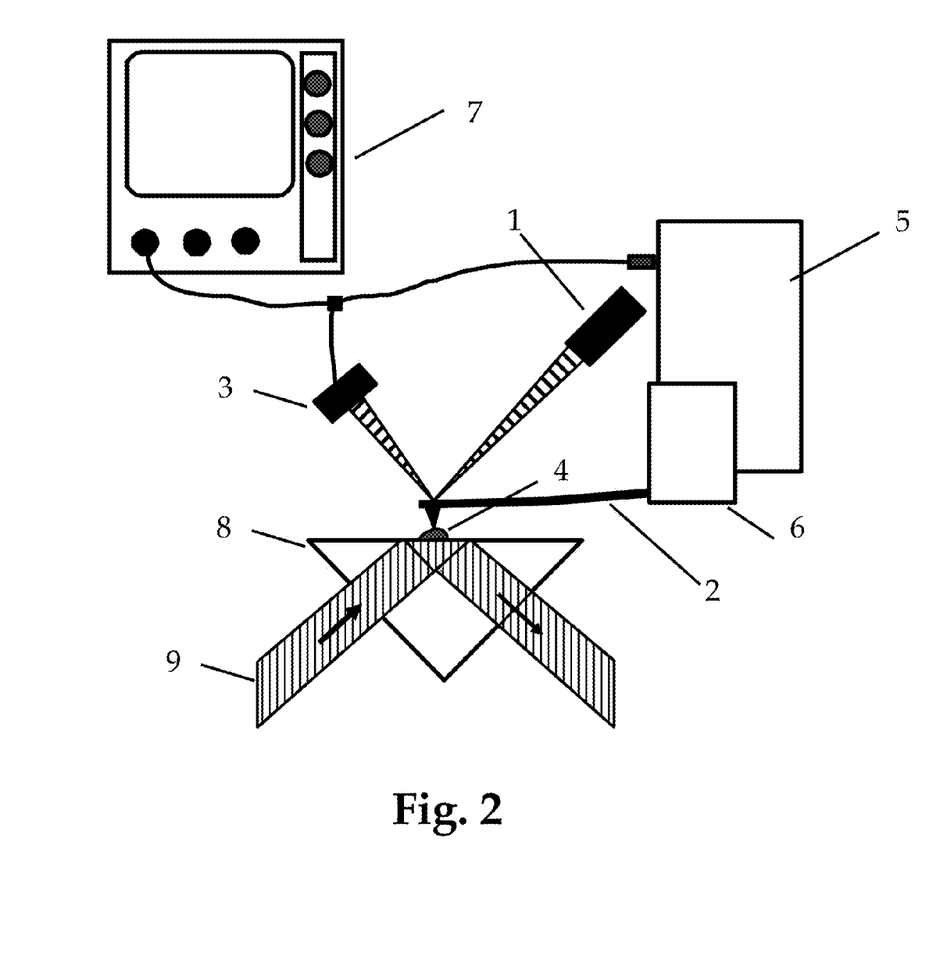

The AFM set-up used for the published work on IR spectroscopy is shown schematically in FIG. 2. In this set-up, the sample 3 is mounted on a ZnSe prism 8, or prism made from other suitable materials, which primarily does not absorb the radiation of interest. A modulated IR source 9 is directed into the prism. In some embodiments the prism is made at an angle such that the beam is in Total Internal Reflection in order for the beam to be propagative in the sample and evanescent in the air. Thus only the sample is significantly exposed to the laser radiation, and the AFM probe 2 is minimally exposed to beam 9. The IR source that is both variable in wavelength and has a pulsed output. The IR source may be pulsed asynchronously or as in the Lu and Belkin paper and copending application Ser. No. 13/236,615, the source may be pulsed at a frequency corresponding to a resonance of the cantilever. The probe 2 is positioned by scanner 6 to interact with a region of the sample. The probe may be held at a desired level of interaction (for example a desired force, cantilever deflection, oscillation amplitude, resonant frequency shift for example) by feedback electronics 5. Feedback electronics can be analog, digital, digital computation any combination of the above. Both the vertical and lateral deflection signal directly from the photo-detector 4, as well as the feedback signal, can be monitored at 7.

Figure 3:
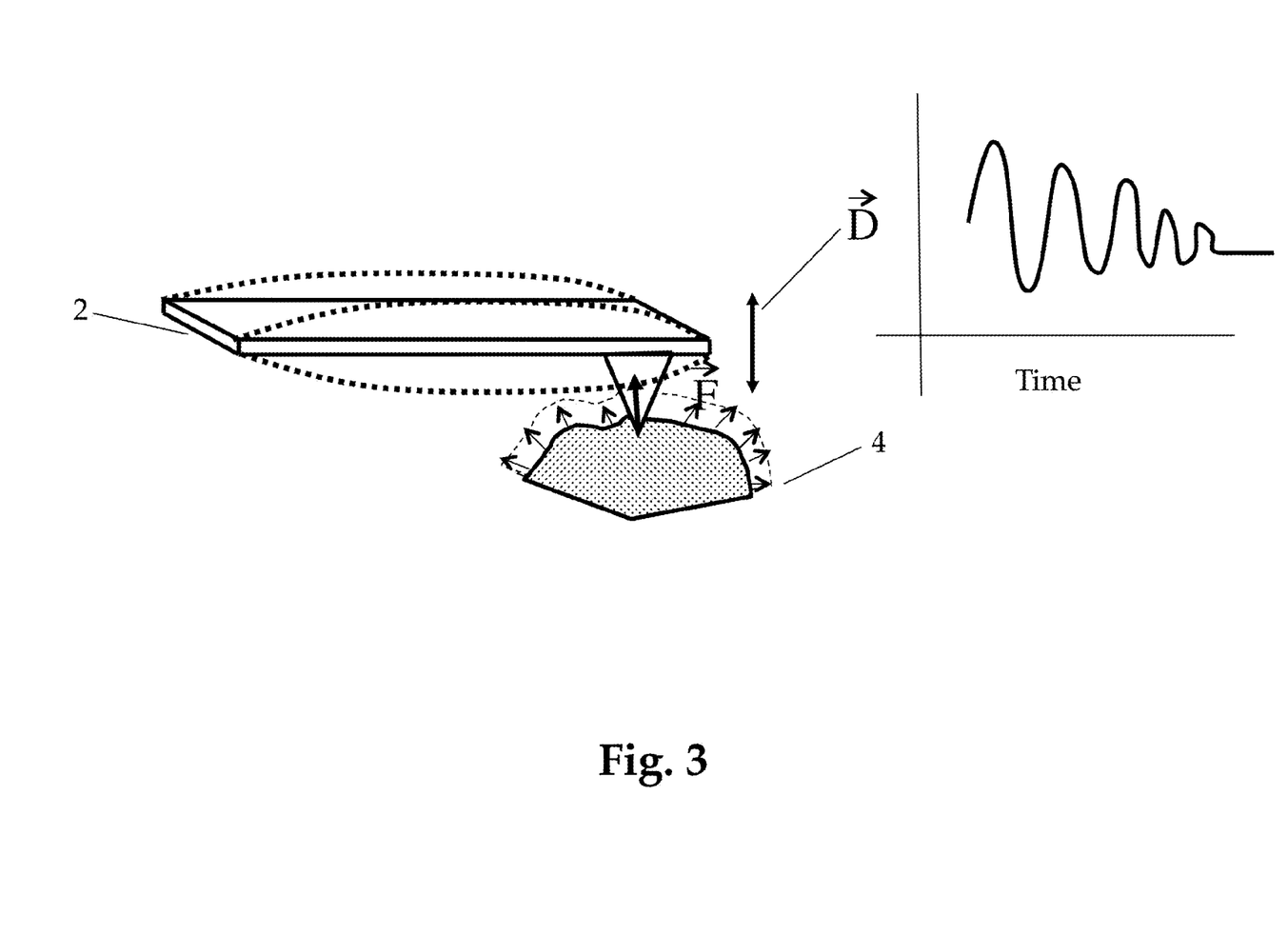

Referring to FIG. 3, when the IR source is pulsed, the sample 3 may absorb some of the energy, resulting in a fast thermal expansion of the sample as shown in the Figure. This has the effect of a quick shock to the cantilever arm 2, which if the ability of the cantilever to respond to this shock is slower than the shock will result in exciting a resonant oscillation in the cantilever arm. In the case of asynchronous pulses with a repetition rate in the kHz range, the shock will result in a decaying oscillation or "ringdown," as shown in the figure. In the case of pulses that are synchronized with a resonance of the cantilever or that have a repetition period shorter than the ringdown decay time, a continuous cantilever oscillation can be generated. Because the IR energy is ideally contained within the sample, this shock is due primarily to rapid sample expansion as minimal IR energy is absorbed by the cantilever itself. In the case of asynchronous IR pulses, transient cantilever response signal is often too fast for the feedback electronics, but can be observed directly from the photodetector. Thus the cantilever rings in the manner shown in FIG. 3 while still in contact with the surface, an effect called "contact resonance". The absolute deflection, amplitude and frequency characteristics of the contact resonance vary with the amount of absorption as well as other properties, such as the local hardness, of the localized area around the probe tip. Also, depending on the direction of the expansion, vertical resonances, lateral resonances or both can be excited. If the tip is to the side of the absorbent material, this will typically cause a stronger lateral response in the cantilever. By repeating the above process at varying wavelengths of the IR source, an absorption spectra on a very localized scale is achieved. By scanning the probe to various points on the sample surface and repeating the spectra measurement, a map of IR spectral surface characteristics can be made. Alternatively, the wavelength of the IR source can be fixed at a wavelength that is characteristic of absorption of one of the components of the sample. The probe can then be scanned across the sample surface and a map of the location of that component can be generated.

The technique is often referred to as PTIR (Photo Thermal Induced Resonance) spectroscopy. A variety of improvements to the technique are disclosed in the parent application to the current application as well as other family members U.S. application Ser. Nos. 12/315,859 and 13/236,666 which are incorporated in their entirety by reference. Among those improvements includes the disclosure of suitable alternative bench top radiation sources to the previously used IR source (a free electron laser) as well as a variety of techniques to improve signal strength and spatial resolution for a variety of samples and applications. For some sample geometries and measurements, more improvement is desirable. It is the object of this invention to provide further enhancement of the PTIR technique for certain sample and measurement scenarios.

BRIEF SUMMARY OF THE INVENTION

The invention is a method of obtaining a measurement of interaction of infrared radiation with a sub-micron region of a sample on a sample substrate with a cantilever probe of a probe microscope b including the steps of:

a. interacting an electric field enhancing tip of the probe microscope with a region of the sample;

b. illuminating the tip and the region of the sample with a source of infrared radiation;

c. enhancing an electric field induced by the infrared radiation in a region surrounding the apex of the tip;

d. measuring a probe response due to the interaction of the enhanced electric field with the sample.

The radiation may also be selected from other wavelength regions including ultraviolet, visible, and terahertz. In other embodiments the probe response is measured at a plurality of wavelengths of the infrared source and/or at a plurality of positions on the sample. Preferably a spatially resolved map is created of a signal indicative of probe response at a plurality of positions on the sample and the map has a spatial resolution of 20 nm or better.

Typically, the detected probe response is due to absorption of infrared radiation by the sample. The probe response may result from thermal expansion of a region of a sample interacting with the tip or alternatively the probe response results from a transient force induced on the tip due to the interaction of the enhanced electric field with the sample. The enhanced electric field may be due to plasmonic enhancement, polaritonic, and/or "lightning rod" effects. In one embodiment, the electric field enhancement results from a metallic coating on at least one of the tip and sample substrate. The metallic coating may be a metal chosen from the list: gold, silver, copper, platinum, and palladium. The enhancing step reduces effects of background absorption from neighboring regions of the sample that are illuminated by the source of infrared radiation but are not interacting with the probe tip apex. In certain embodiments, the sample is <20 nm in thickness.

In certain other embodiments, the source of IR radiation comprises a pulsed source and in some cases, the source of IR radiation produces a pulse at the sample with an energy of less than 100 nanojoules and even less than 5 nJ. In other embodiments, the source of IR radiation is a quantum cascade laser or is an optical parametric oscillator or a globar/FTIR source. In some embodiments, the infrared radiation is pulsed, and may be at a fluence of $10^{-3}$ J/cm$^2$ per pulse.

In some embodiments the radiation is modulated at a frequency substantially corresponding to a resonant frequency of the cantilever probe. Preferably, the resonant frequency substantially corresponds to a contact resonant frequency of the cantilever probe.

In some embodiments, the illuminating and enhancing steps induce a substantially continuous resonant oscillation of the cantilever probe when the infrared source is tuned to a wavelength corresponding to an infrared absorption in the sample. The probe response may be resonantly enhanced by a quality factor (Q) of the cantilever probe and in some cases the cantilever quality factor is at least 30. The methods may include measuring a signal indicative of at least one of the amplitude, phase and frequency of the substantially continuous oscillation. In other embodiments, the infrared radiation is substantially polarized in a transverse magnetic (TM) mode.

In other embodiments the probe response is a transient decaying oscillation. A signal may be measured indicative of at least one of an amplitude, phase, frequency, and decay time of the transient decaying oscillation.

BRIEF DESCRIPTION OF THE DRAWINGS

The invention will be better understood by referring to the accompanying Figures.

FIG. 2 shows schematically the set-up the laboratory version of the spectroscopy technique FIG. 3 schematically shows the effect on the cantilever arm when the sample absorbs pulsed IR energy FIG. 4 schematically shows a PTIR system where tip electric field enhancement takes place.

FIGS. 8a, b and c illustrate the differences in illuminated area for various versions of PTIR configuration.

DETAILED DESCRIPTION OF THE INVENTION

For review, referring to FIG. 3, sample 4 is illuminated by a beam of radiation from a tunable radiation source 9. In a preferred embodiment radiation from the source is modulated, either within the source itself or using an external modulator. When radiation interacts with the sample, the sample can respond to the illumination. In the case of absorption of the radiation the sample can heat up and undergo thermal expansion. Cantilever 2 is affected by the response of the sample triggering a probe response. The probe response will depend on both the form of the illumination and the properties of the sample. In the case of a pulsed source where the wavelength of the infrared source is tuned to an absorption of the sample, the absorbed radiation will cause rapid heating and thermal expansion of the sample. The thermal expansion then causes a force impulse at the apex of the AFM probe tip. The force impulse can generate a transient oscillatory response of the cantilever (also called a "ringdown." In the case the source is continuously modulated, for example with a sinusoidal oscillator, the probe response can be a substantially continuous oscillation when the infrared source is tuned to an absorbing wavelength of the sample. Note that by substantially continuous oscillation, we do not mean constant amplitude. In fact, the amount of probe response (ringdown or continuous oscillation) depends on the strength of the absorption of the sample and the strength of the radiation source at a given wavelength. Measuring the probe response as a function of wavelength (or equivalently as a function of energy, frequency, or wavenumber) can provide a signature of a specific material, for example an absorption spectrum. This is the basis of the PTIR technique, leading to the capability to provide spectral information about the composition of a sample surface with very high spatial resolution.

The IR source originally used in the laboratory set-up described above was a free electron laser (FEL). An FEL is one of the few IR sources that can be continuously tuned across wavelength, as is necessary to generate a spectrum. However, other than this attribute an FEL is poor choice in every other way. They are large expensive and complex devices, only existing in a few locations in the world. Therefore they are totally impractical as a source for a commercial version of the technique. Moreover they are limited as to rep rate. Therefore other sources such as an Optical Parametric Oscillator (OPO) or tunable Quantum Cascade Laser (QCL) and/or globar source could be used. OPO's convert monochromatic laser radiation (pump) into a tunable output via a three-wave mixing process with quantum conversion efficiencies that can exceed 50%. The heart of an OPO is a nonlinear-optical crystal. In this crystal, the pump photon decays into two less energetic photons (signal and idler) so that the sum of their energies is equal to that of the pump photon. By careful design of the crystal it is possible to change the wavelength of the IR radiation by moving the crystal and/or controlling its temperature. More than one crystal is typically needed to cover the full mid-IR range. Additional disclosure about OPO's as applied to PTIR systems can be found in incorporated reference U.S. Ser. No. 12/315,859. Disclosure about QCL's can be found in incorporated reference U.S. Ser. No. 13/236,115. Globar sources are thermal sources, typically employing a filament heated to high temperatures to emit radiation over a broad range of wavelengths. Globars are commonly used in Fourier Transform Infrared Spectrometers (FTIR). Other infrared sources that can be either internally or externally modulated may also be suitable. In an alternate embodiment, the PTIR technique can employ sources outside the infrared, for example in the ultraviolet, visible, near-IR, and terahertz regions. Many pulsed and modulatable sources exist in these wavelength ranges. In the UV, visible and near IR, diode laser systems exist that can be operated in modulated or pulsed mode. In UV, near-IR, visible and IR a variety of pulsed laser sources exist that use optical parametric oscillators, optical parametric generation, sum-frequency generation, second harmonic generation, frequency combs and related techniques. In the terahertz region QCLs are becoming available (some have been fabricated by inventor Mikhail Belkin's lab, for example.) Supercontinuum sources also provide the option for using very short pulsed that contain a broad wavelength spectrum within a single pulse. Fourier transform techniques can be used to extract the wavelength dependent sample response using globar or supercontinuum sources.

The inventors have also found that more signal can be generated if the IR source is modulated at or near the resonant frequency of the lever, effectively creating a driven oscillator as opposed to a decaying oscillation. This technique is described in detail in incorporated reference U.S. Ser. No. 13/236,115. For this mode of operation, a QCL is a particularly suitable source as QCL repetition rates are potentially higher and therefore can be used with stiffer, higher resonant frequency probes, which may be suitable for certain applications.

In the incorporated references, both bottom up illumination of the tip and sample as well as top down illumination schemes are discussed. Top down schemes are preferable to the bottom up approach of a sample mounted on a prism for a variety of reasons. For the prism mount approach, a sample specimen must be cut and thinned to fit the prism and be at least partially transparent in the IR. For such a sample, absorption takes place throughout the sample and any expansion detected by the probe tip may be due to influences away from the vicinity of the probe, thus blurring out spatial resolution. Relatively, for top down illumination, both the physical aspects of sample, size, shape, and sample transparency are less constrained.

However top down PTIR techniques (and bottom up as well) suffer from the fact that radiation is incident over an area of many square microns (IR spot size) and energy absorbed away from the probe tip can conduct to the tip-sample contact area creating unwanted background effects. Basically at illumination power levels sufficient to cause measurable probe interactions the absorption depth of IR radiation is in the range of many microns for typical absorption peaks. This means that the signal detected by the probe can be the result of thermal expansion of materials very far below from the tip. Moreover at required illumination power levels, the heating and expansion effects away from the tip measurably affect more of the AFM probe than just the tip itself, further blurring spatial resolution.

The inventors have determined that near-field tip enhancement can, for certain scenarios greatly improve PTIR spatial resolution. When radiation strikes a conductor with a small radius of curvature, i.e. the tip of a metal coated or other electrically active AFM probe tip, the fields are enhanced by an order of magnitude or more in a small region near the tip apex. The intensified field acts on the sample over a region comparable to the tip radius. This effect is used in other techniques where the enhanced fields are detected in the far field, for example tip-scattering near field optical microscopy (s-SNOM) and tip-enhanced Raman spectroscopy (TERS). In both of these techniques, however, the radiation scattered from the the tip-sample region must be discriminated from a usually larger background of radiation scattered from neighboring regions of the sample. When applied to PTIR, the enhanced field induced a higher intensity right at the tip where the force is directly transduced to the AFM cantilever, effectively amplifying the illumination in a very small region right at the tip where the sample interaction to the illumination is measured. Thus to get the same measurable effect in the region of the tip, far lower illumination power levels need be used, which greatly reduce the background and long scale absorption issues described above.

The mechanical resonance frequencies of the AFM cantilever depend on the cantilever type as well as AFM scan parameters (e.g., force) and sample properties. To benefit from the cantilever-resonance enhancement described above, we need to have short-pulse mid-IR sources that can operate at high (10 kHz-1 MHz) and easily adjustable repetition rates. Tunable mid-infrared QCLs are well suited for that task. However, their pulse energy is orders of magnitude smaller than that provided by free-electron lasers and OPOs used for previous AFM-IR experiments. In particular, tunable QCLs used by the inventors can provide 50 ns pulses with pulse energies ~5 nJ which gives a pulse fluence of ~$10^{-5}$ J/cm$^2$ on sample surface, while OPOs used in commercial AFM-IR instruments available from Anasys Instruments and previously in the free-electron are in the range of ~5 µJ/pulse of broadly-tunable mid-IR radiation and produced pulse fluence of $10^{-1}$-$10^{-2}$ J/cm$^2$ per pulse on sample surface. (A co-pending application describes techniques for dynamically adjusting IR source power levels to optimize sensitivity and reduce sample damage.) As a result, despite benefiting from cantilever-resonance signal enhancement, the sensitivity of the QCL setup can be similar to that described by Dazzi et al and available commercially from assignee Anasys. We note, however, that the sample heating in experiments in F. Lu, and M. A. Belkin, "Infrared absorption nano-spectroscopy using sample photoexpansion induced by tunable quantum cascade lasers," *Optics Express* 19, 19942 (2011), was only 10 mK, compared to 1-50K reported in publications by Dazzi et al. To increase the sensitivity of QCL-based AFM-IR setup and ultimately achieve AFM-IR nanospectroscopy with sub 20 nm sensitivity, we use plasmonic or other light-intensity enhancement at the end of the AFM tip. It has been demonstrated that metal nanoparticles, sharp metal tips, and optical antenna structures may enhance radiation field intensity by 2-4 orders of magnitude. A high-intensity region can be localized within 10 nm-diameter or smaller spots. (See for example K. B. Crozier, A. Sundaramurthy, G. S. Kino, and C. F. Quat, "Optical antennas: Resonators for local field enhancement," J. Appl. Phys. 94, 4632 (2003) and references therein and N. Yu, E. Cubukcu, L. Diehl, M. A. Belkin, K. B. Crozier, F. Capasso, D. Bour, S. Corzine, G. Höfler, "Plasmonic quantum cascade laser antenna," Appl. Phys. Lett. 91, 173113 (2007).)

Figure 4:
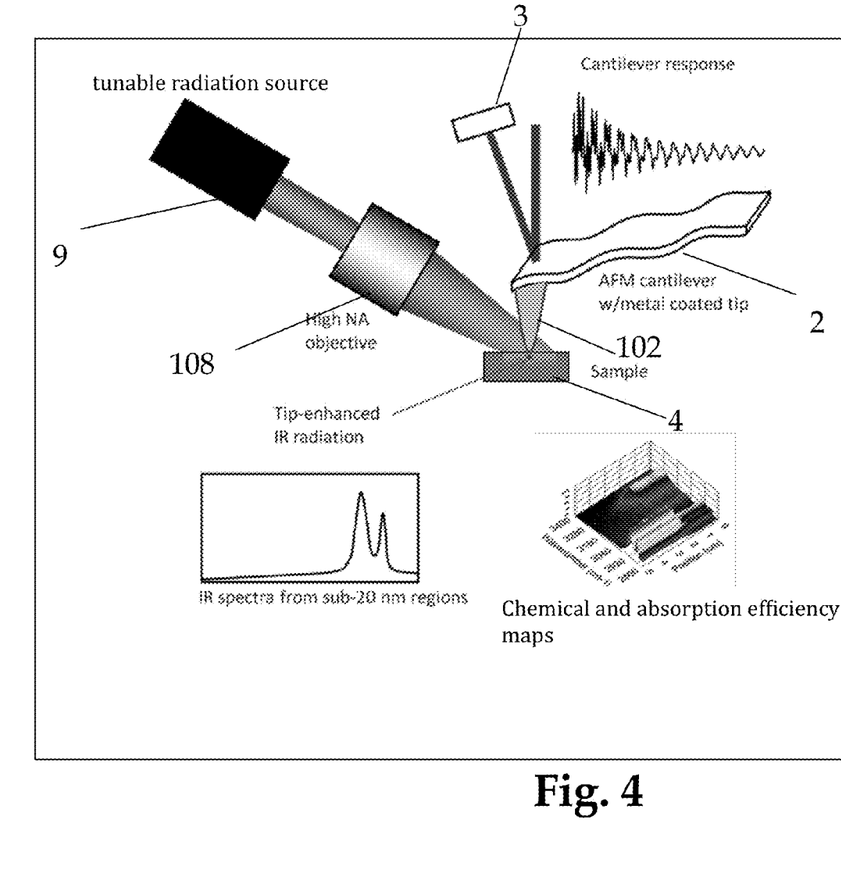
Figure 8:
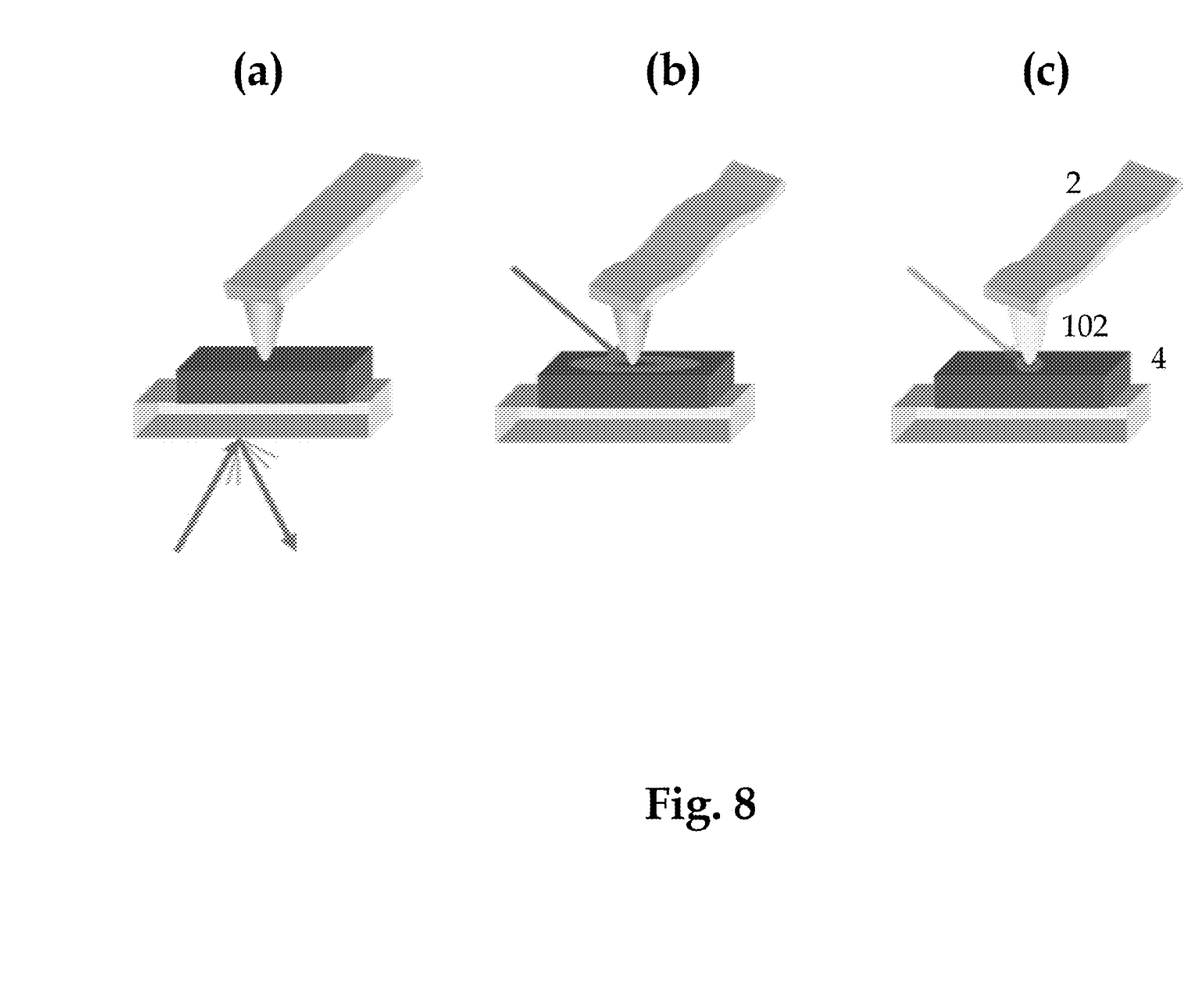
Figure 9:
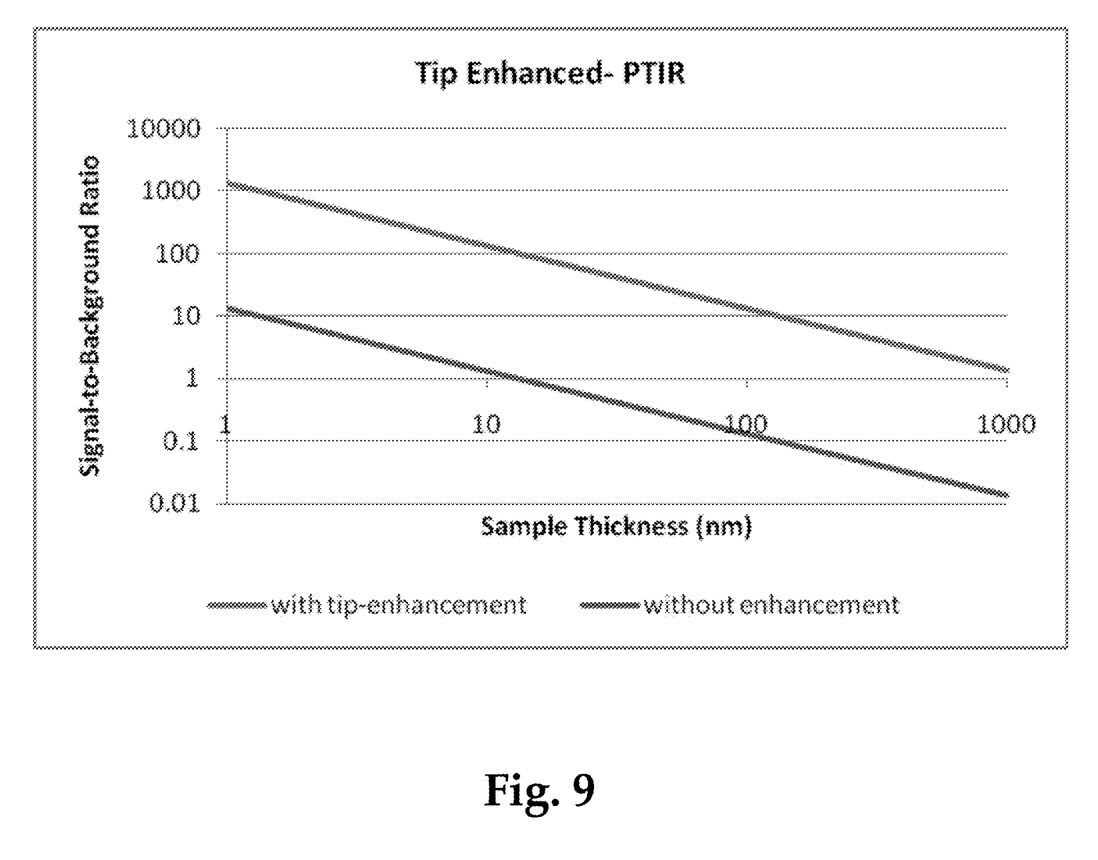
FIG. 9 shows an example improvement of the signal-to-background ratio of tip-enhanced vs non-tip enhanced PTIR as a function of sample thickness.

Referring to FIG. 4, a PTIR system according to the invention is shown. Probe 2 has an electric field enhancing tip 102. This tip may be made enhancing in a variety of ways, most easily by simply adding a metal coating step to the tip manufacturing process that applies a coating in the tip region. Many metals and other conductors can provide electric field enhancement due to electric field concentration around the sharp features of the tip apex, i.e. the "lightning rod effect." Other probe materials or doping process could also be employed to create a conductive region at the tip. Certain materials can further enhance the electric field around the tip-sample region due to plasmonic, polaritonic, and/or antenna resonance effects. In this case the metal coating can provide a resonance at frequencies corresponding to the optical frequencies of the incident radiation employed. Suitable metals may include gold, silver, copper, platinum, and palladium. Source 9 is focused by optics 108 on to sample 4 in a spot at the tip. Electric field enhancement, such as plasmonic enhancement will effectively increase the intensity of the illumination right at the tip. FIG. 8 qualitatively shows the improvement over prior art bottom up (8*a*) and top down (8*b*) PTIR compared to tip enhanced (8*c*) PTIR.

Figure 5:
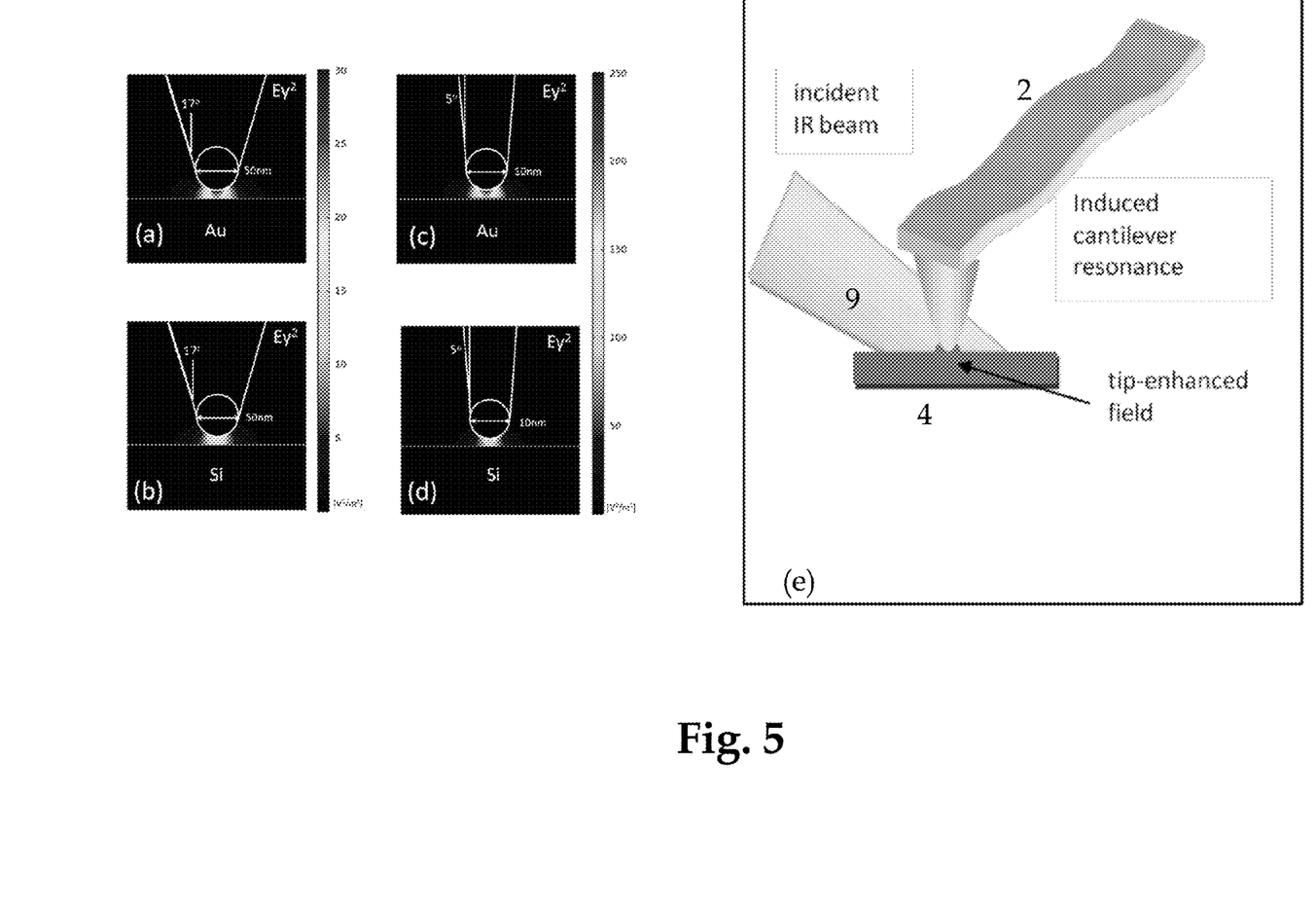
FIG. 5 shows models of electric field enhancement in the vicinity of the apex of the tip at two tip radii for coated vs normal probe tips.

FIG. 5 shows the results of simulations of electric field enhancements in the vicinity of a probe apex of a gold-coated AFM tip. Local field enhancements are shown at the end of the gold-coated AFM tip with 50 nm-diameter (a,b) and 10 nm-diameter (c,d) apex. Note different intensity scalebars for (a,b) and (c,d). Simulations are performed with COMSOL Multiphysics. P-polarized light at λ=8.5 µm is incident at 70° angle and has $E_y$ field component (y-axis is normal to the surface of the substrate) of 1 V/m far away from the tip. Under the tip, the field intensity and light intensity (approximately ~$|E_y|^2$) is enhanced. We obtain ~25 times light intensity enhancement for 50 nm-appex tip 10 nanometers above gold-coated substrate (a), 10-15 times intensity enhancement for 50 nm-appex tip 10 nanometers above the uncoated silicon substrate (b), over 200 times enhancement for 10 nm apex tip 2 nm above gold-coated substrate (c), and ~100 times intensity enhancement for 10 nm-appex tip 2 nanometers above the uncoated silicon substrate (d). Similar enhancements are obtained for other light wavelengths in the range 1/λ=4000-600 cm$^{-1}$.

Thus lower illumination power 9 is required to produce high intensity field right below the AFM tip 2 see FIG. 5. With the enhancement figure shown, it is possible to use significantly lower energy/power from the source of IR radiation. Thus is is possible to use much lower energy/power than without the tip-enhancement to achieve the same temperature rise in the sample. Combined with resonance enhancement of the cantilever, it is possible to also adequately measure probe response with significantly smaller sample temperature increases. For example, the inventors have achieved acceptable results with temperature rises estimated to be <10 mK as shown in F. Lu, and M. A. Belkin, "Infrared absorption nano-spectroscopy using sample photoexpansion induced by tunable quantum cascade lasers," *Optics Express* 19, 19942 (2011). In the simulations shown in FIG. 5, the best results are obtained for sharp (10 nm-appex) gold-coated tips 2 close to a gold-coated substrate. The sample 4 is positioned between the tip 2 and the substrate and is assumed to have refractive index of 1.5. Over 200 times light intensity enhancement is expected in case shown in FIG. 5(*d*). We note that even higher enhancement factors are possible for sharper metal tips (apex smaller than 10 nm) and optical antennas. We also emphasize that ever with 200 times of intensity enhancement, the sample heating during the laser pulse in a QCL-based PTIR microscopy setup in F. Lu, and M. A. Belkin, "Infrared absorption nano-spectroscopy using sample photoexpansion induced by tunable quantum cascade lasers," *Optics Express* 19, 19942 (2011),is expected to be only ~2° K (=10 mK×200). The plasmonic enhancement will provide two orders of magnitude or higher boost in sensitivity of the technique that was demonstrated in F. Lu, and M. A. Belkin, "Infrared absorption nano-spectroscopy using sample photoexpansion induced by tunable quantum cascade lasers," *Optics Express* 19, 19942 (2011).

The inventors have found that this technique coupled with the technique of modulating the IR source at or near the contact resonance of the cantilever is especially advantageous. Quantum cascade lasers (QCLs) are advantageous sources for this reason since their repetition rate can be exceed 1 MHz. Optical parametric oscillators (OPOs) are also suitable for many cases. Broadband sources can also be used, including globar sources (for example those used in conventional Fourier Transform Infrared Spectroscopy (FTIR). In the case of a globar/FTIR source it is desirable to add an additional modulation to either pulse or continuously modulate the beam power. Suitable modulators may include polygonal mirrors, high speed choppers or shutters, electro-optic modulators, photoacoustic modulators, photoelastic modulators and/or any other device that can modulate the power of infrared radiation delivered to the sample region. Most of the previous PTIR teachings apply. Source illumination can be varied over wavelengths of interest to obtain spectral information about the sample surface and the sample/tip can be translated laterally to map the surface, thus creating high resolution spectral maps of sample composition. Top down illumination becomes practical for a wider variety of samples.

Figure 6:
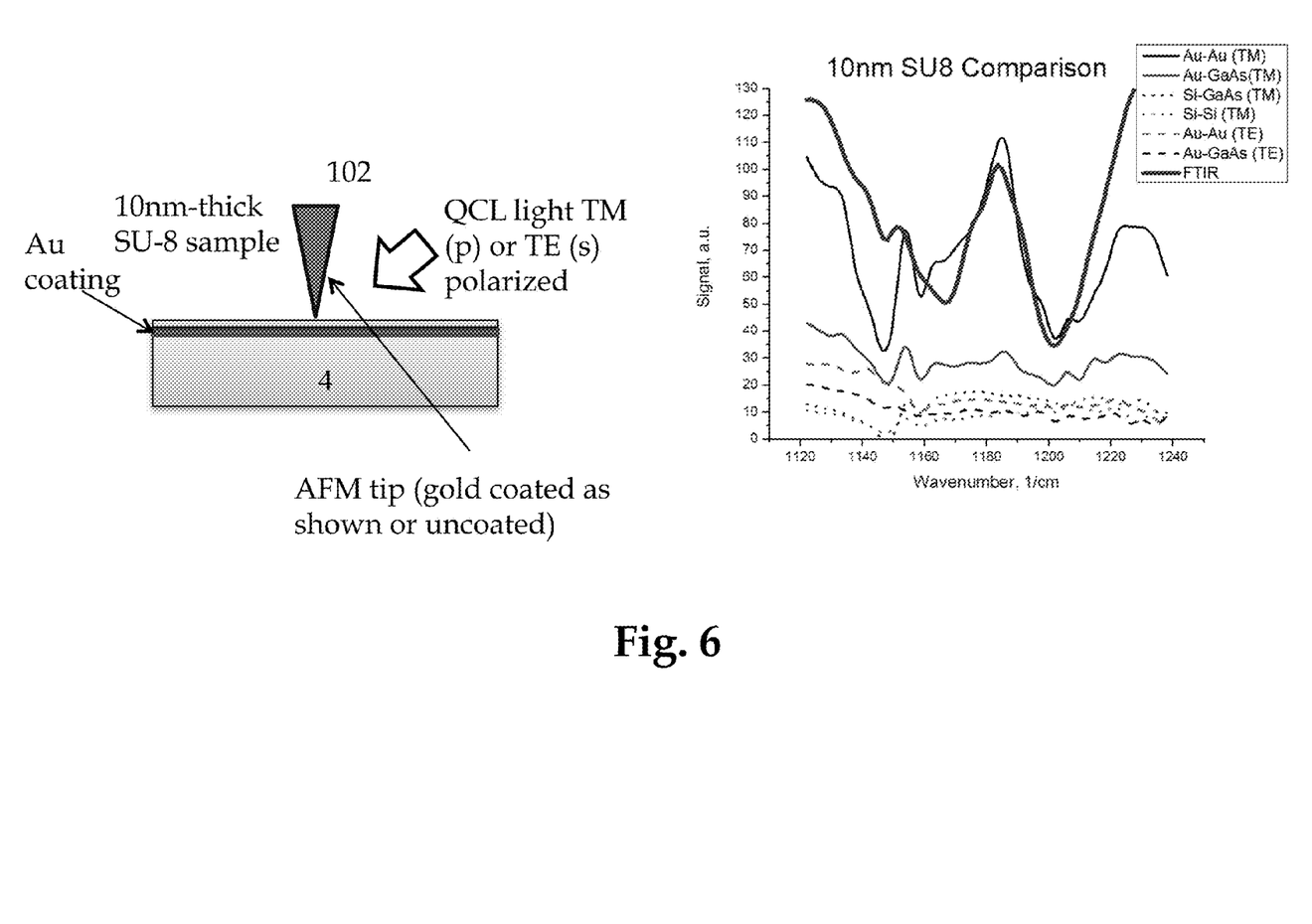
FIG. 6 shows an infrared absorption spectrum obtained under the current invention of a 10 nm thick film with and without optimized tip-enhanced PTIR.
Figure 7:
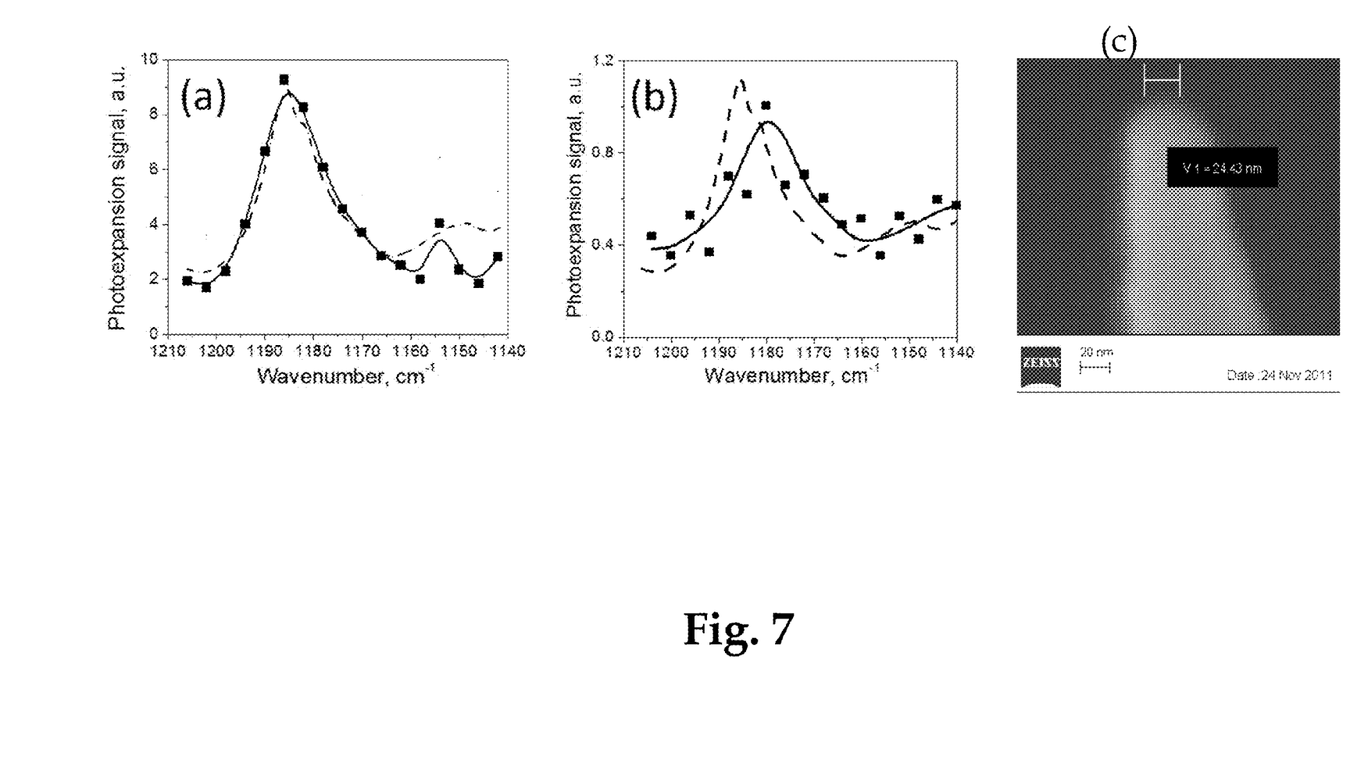
FIG. 7 also shows results for tip enhanced vs non-tip enhanced PTIR on a film.

Preliminary results shown in FIGS. 6 and 7 justify the advantage of plasmonic-enhancement approach. Regular silicon AFM tip was coated with 50 nm-thick layer of gold. We estimate the tip apex diameter to be 50 nm, see FIG. 7(c). 10 nm-thick layer of SU-8 was positioned on gold-coated silicon substrate. From FIG. 5(a) we expect the AFM tip to provide ~25 times intensity enhancement. Sample was illuminated by tunable QCL pulses from the top of the substrate. The AFM-IR spectrum of 10-nm-thick film of SU-8 obtained in this experimental configuration are shown in FIG. 7 (a). In comparison, FIG. 7(b) reproduces the photoexpansion spectrum of a five times thicker (50 nm-thick) film of SU-8 obtained with AFM-IR without using plasmonic enhancement in F. Lu, and M. A. Belkin, "Infrared absorption nano-spectroscopy using sample photoexpansion induced by tunable quantum cascade lasers," *Optics Express* 19, 19942 (2011). The FTIR spectrum of SU-8 is shown by dashed line in both FIGS. 7(a) and 7(b). Clearly, the AFM-IR spectrum in FIG. 7(a) has much higher signal-to-noise ratio, compared to that in FIG. 7(b), and is in nearly perfect agreement with the FTIR spectrum of SU-8.

Another key advantage of using plasmonic or other field enhancement in AFM-IR microscopy is improvements in spatial resolution. The spatial resolution of traditional PTIR microscopy is determined by thermal diffusion length in the sample. With plasmonic enhancement, high-intensity 'hot spot' is localized within 10 nm of less of AFM tip, see FIG. 5. Sample photo-expansion will only occur if absorbing region of the sample is located within the 'hot spot'. As soon as the absorbing region of the sample is outside of the 'hot spot' at the end of the AFM tip, sample will not absorb any significant amount of optical energy and no photoexpansion occurs. Thus, the spatial resolution of 'plasmonic-enhanced' AFM-IR is determined by the dimension of the plasmonic hot spot and not by thermal diffusion length in samples. This is particularly important for samples with high thermal diffusion (e.g., for crystalline samples).

Another advantage of the tip-enhanced approach is that it enhances detection in a very small area near the tip-sample contact, paving the way for the use of a much broader array of samples and sample substrate. In the current PTIR technique samples are mounted on ZnSe prisms and the IR radiation is brought in from under the sample through total internal reflection illumination. The current illumination arrangement prevents us from applying the AFM-IR technique to thick samples or samples prepared on substrates other than the ZnSe prism. To overcome this in the current invention, we can bring in the IR radiation from the top side of the sample. Without tip-enhancement or other techniques for localizing the detection of the IR absorption spatial resolution may be compromised. The issue comes from the fact that for many polymer materials, the absorption depth of IR radiation is in the range of many microns for typical absorption peaks. This means that the signal detected by the cantilever can be the result of thermal expansion of materials very far below from the tip. Employing the near-field tip enhancement allow the use of much lower intensity IR radiation, thus dramatically reducing the background due to radiation absorbed by the sample away from the tip-sample contact. For example, near-field tip enhancement can increase the local field by a factor of 10, and thus the incident energy by 100× near the tip apex.

FIG. 1 shows an estimate of signal-to-background ratio for tip-enhanced PTIR calculated for a 10 nm tip as a function of sample thickness. A 100 nm photovoltaic film will have a signal-to-background ratio >10 with the tip-enhanced PTIR instrumentation.

FTIR-Based Plasmonic-Enhanced AFM-IR Nanospectroscopy

QCLs can currently operate at room temperature in 3.3-15 µm (3000-600 cm$^{-1}$) spectral range. A single QCL can be tuned by over 400 cm$^{-1}$ around nearly any center wavelength in that range. A set of 6 QCLs can cover almost entire molecular fingerprint region. However, QCL-based AFM-IR approach has some disadvantages such as high system cost and difficulty addressing 4000-3000 cm$^{-1}$ spectral region.

An alternative FTIR-based AFM-IR setup is another solution. A typical Globar source in a FTIR outputs only ≈20 mW of useful thermal radiation. This radiation can be focused to ~100 µm-radius spot, which is similar to that used in the inventors' QCL-based setup. The thermal emission spectrum spans the entire molecular fingerprint region. However, only a small fraction of this power falls within absorption bands of a typical polymer sample.

FIG. 6(b) shows the absorption spectrum of 50 µm-thick polystyrene film with the horizontal dark line showing the absorbance of 25 µm-thick SU-8 film at 1185 cm$^{-1}$ (probed by AFM-IR in FIG. 8). We estimate that only 5% of thermal radiation between 600 and 4000 cm$^{-1}$ fall within absorption bands of polystyrene that are at least ½ as strong as that of SU-8 at 1185 cm$^{-1}$. This means that only 0.6 mW of ≈20 mW of useful thermal power will fall within strong absorption bands of polystyrene.

Figure 10:
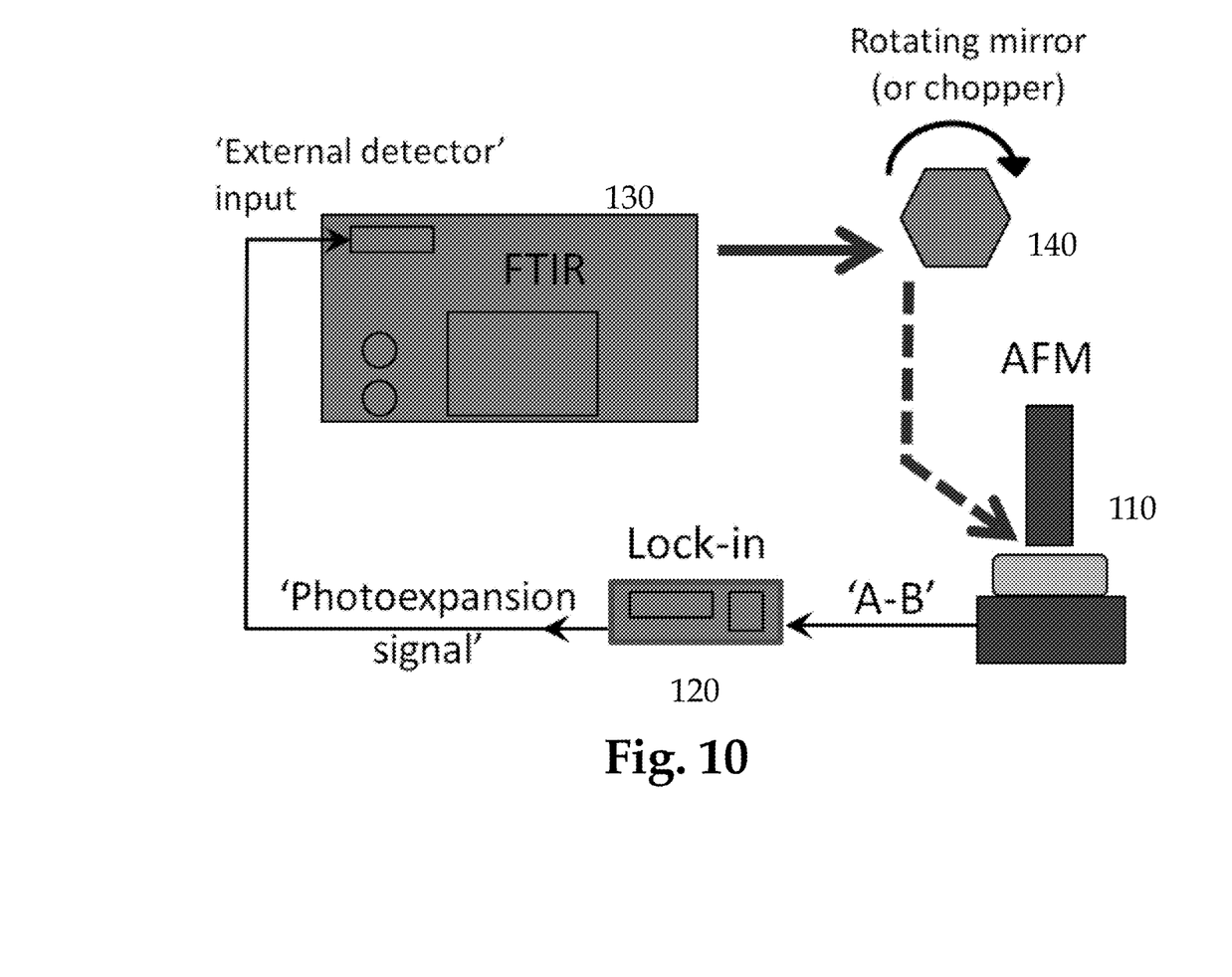
FIG. 10 is a simplified schematic diagram of an embodiment of the current invention using a modulated beam from a FTIR or other thermal source.

FIG. 10 shows an embodiment of the current invention in which a thermal source, for example a globar or even a commercial FTIR 130 is used as the source of IR radiation. To produce pulses of thermal radiation at cantilever resonance frequency, the Globar output of an FTIR can be modulated at ~100 kHz by either, e.g., by a rotating mirror (available, e.g., from Lincoln Laser, Inc) or a fast mechanical chopper (available, e.g., from Scitech Instruments) 140. If the cantilever has a resonance frequency $u_0$≈50 kHz and Globar output is modulated at 50% duty cycle (pulse length ≈10 µs). Assuming 0.6 mW of Globar radiation that hits molecular absorption lines, pulse length of ≈10 µs, and taking into account that only ½ of thermal power has the required p-polarization for plasmonic enhancement, we obtain that ≈3 nJ of p-polarized energy per pulse will hit absorption lines of our sample. This amount is comparable to 4 nJ of QCL pulse energy used in our experiments outlined above that produced spectrum shown in FIGS. 7(a). We thus expect that modulated Globar output will produce sufficient photothermal expansion to produce detectable response in AFM-IR technique even for samples at thin as 10 nm. We note that we expect to achieve further improvements in sensitivity of AMF-IR microscopy over the course of this project by using higher Q-factor cantilevers and sharper metal tips that produce higher plasmonic intensity enhancement.

A pulse length of 10 µs in prior art PTIR could translate into a loss of spatial resolution due to the thermal diffusion. Using values for typical polymers and biological samples, a pulse of 10 µs would suggest a thermal diffusion length of ≈1.5 µm and even larger for crystalline samples with high thermal diffusivity, which is insufficient for nanospectroscopy. However, as discussed above, the resolution of the AFM-IR setup with plasmonic or other tip-based field enhancement is independent of the diffusion length and is instead determined by the dimensions of the 'hot spot' at the end of the AFM tip, which can be below 10 nm, see, e.g., FIG. 5. Thus, our plasmonic-enhanced FTIR-based AFM-IR technique can have nanoscale resolution.

A simplified optical setup for FTIR-based tip-enhanced AFM-IR microscopy is shown in FIG. 10. Thermal radiation is output from FTIR 130 external output port, it is then modulated 140 and sent to the AFM-IR setup 110; cantilever 'A-B' deflection signal is sent to lock-in amplifier 120; the 'photo-expansion signal' output from the lock-in is sent into 'external detector' input of the FTIR. Spectra from can then be obtained using the conventional FTIR software, but with spatial resolution orders of magnitude better than conventional FTIRs.

We claim:

1. A method of obtaining a measurement of interaction of infrared radiation with a sub-micron region of a sample on a sample substrate with a cantilever probe of a probe microscope, the method comprising:
   a. interacting an electric field enhancing tip of the probe microscope with a region of the sample;
   b. illuminating the tip and the region of the sample with a source of modulated infrared radiation;
   c. enhancing an electric field induced by the infrared radiation in a region surrounding the apex of the tip;
   d. measuring a probe response due to the interaction of the enhanced electric field with the sample.

2. The method of claim 1 wherein the enhanced electric field is due to at least one of plasmonic enhancement, polaritonic enhancement, and lightning rod effect.

3. The method of claim 1 wherein the detected probe response is due to absorption of infrared radiation by the sample.

4. The method of claim 1 wherein the electric field enhancement results from a metallic coating on at least one of the tip and sample substrate.

5. The method of claim 3 wherein the metallic coating comprises a metal chosen from the list: gold, silver, copper, platinum, and palladium.

6. The method of claim 1 wherein the source of modulated infrared radiation is modulated at a frequency substantially corresponding to a resonant frequency of the cantilever probe.

7. The method of claim 6 wherein the resonant frequency substantially corresponds to a contact resonant frequency of the cantilever probe.

8. The method of claim 1 wherein the source of IR radiation is a quantum cascade laser.

9. The method of claim 1 wherein the source of infrared radiation is an optical parametric oscillator.

10. The method of claim 1 wherein the source of infrared radiation comprises at least one of a globar and a Fourier Transform Infrared Spectrometer.

11. The method of claim 1 wherein source of IR radiation comprises a pulsed source.

12. The method of claim 11 wherein the source of IR radiation produces a pulse at the sample with a fluence of $10^{-3}$ J/cm$^2$ per pulse.

13. The method of claim 1 further comprising the step of measuring the probe response at a plurality of wavelengths of the infrared source.

14. The method of claim 1 further comprising the step of measuring the probe response at a plurality of positions on the sample.

15. The method of claim 14 further comprising the step of creating a spatially resolved map of a signal indicative of probe response at a plurality of positions on the sample wherein the map has a spatial resolution of 20 nm or better.

16. The method of claim 1 wherein the enhancing step reduces effects of background absorption from neighboring regions of the sample that are illuminated by the source of infrared radiation but are not interacting with the probe tip apex.

17. The method of claim 1 wherein the source of IR radiation comprises a pulsed source and wherein the source of IR radiation produces a pulse at the sample with an energy of less than 100 nanojoules and preferably less than 5 nJ.

18. The method of claim 1 wherein the illuminating and enhancing steps induce a substantially continuous resonant oscillation of the cantilever probe when the infrared source is tuned to a wavelength corresponding to an infrared absorption in the sample.

19. The method of claim 18 wherein the probe response is resonantly enhanced by a quality factor (Q) of the cantilever probe.

20. The method of claim 19 wherein the cantilever quality factor is at least 30.

21. The method of claim 1 wherein the probe response results from thermal expansion of a region of a sample interacting with the tip.

22. The method of claim 1 wherein the probe response results from a transient force induced on the tip due to the interaction of the enhanced electric field with the sample.

23. The method of claim 1 wherein the infrared radiation is substantially polarized in a transverse magnetic (TM) mode.

24. The method of claim 1 wherein the sample is <20 nm in thickness.

25. The method of claim 1 wherein the probe response is a transient decaying oscillation.

26. The method of claim 25 further comprising the step of measuring a signal indicative of at least one of an amplitude, phase, frequency, and decay time of the transient decaying oscillation.

27. The method of claim 1 wherein the probe response is a substantially continuous oscillation when the infrared source is tuned to a wavelength corresponding to an infrared absorption of the sample.

28. The method of claim 27 further comprising the step of measuring a signal indicative of at least one of the amplitude, phase and frequency of the substantially continuous oscillation.

29. A method of obtaining a measurement of interaction of radiation with a sub-micron region of a sample on a sample substrate with a cantilever probe of a probe microscope, the method comprising:
   a. interacting an electric field enhancing tip of the probe microscope with a region of the sample;
   b. illuminating the tip and the region of the sample with a source of modulated radiation;
   c. enhancing an electric field induced by the radiation in a region surrounding the apex of the tip;
   d. measuring a probe response due to the interaction of the enhanced electric field with the sample.

30. The method of claim 29 wherein the radiation is selected from a wavelength region including ultraviolet, visible, infrared and terahertz.

* * * * *